(12) United States Patent
Pettersson et al.

(10) Patent No.: US 6,761,910 B1
(45) Date of Patent: Jul. 13, 2004

(54) PHARMACEUTICAL COMPOSITION FOR THE TREATMENT OF ACUTE DISORDERS

(75) Inventors: Anders Pettersson, Kode (SE); Christer Nystrom, Uppsala (SE)

(73) Assignee: Diabact AB, Uppsala (SE)

( * ) Notice: Subject to any disclaimer, the term of this patent is extended or adjusted under 35 U.S.C. 154(b) by 0 days.

(21) Appl. No.: 09/787,888

(22) PCT Filed: Sep. 24, 1999

(86) PCT No.: PCT/SE99/01687

§ 371 (c)(1),
(2), (4) Date: Jun. 8, 2001

(87) PCT Pub. No.: WO00/16750

PCT Pub. Date: Mar. 30, 2000

(30) Foreign Application Priority Data

Sep. 24, 1998 (SE) .............................................. 9803240

(51) Int. Cl.[7] .............................. A61K 9/14; A61K 9/16; A61K 9/50
(52) U.S. Cl. ..................... 424/489; 424/490; 424/500; 424/492; 424/493; 424/494; 424/496; 424/497; 424/435
(58) Field of Search .............................. 424/440, 441, 424/434, 435, 485, 489, 490, 500

(56) References Cited

U.S. PATENT DOCUMENTS 5,288,498 A * 2/1994 Stanley et al. .............. 424/440

FOREIGN PATENT DOCUMENTS

| EP | 0 144 243 | 6/1985 | |
|---|---|---|---|
| EP | 0 324 725 A1 * | 1/1989 | ............ A61K/9/18 |
| EP | 0 324 725 | 7/1989 | |

OTHER PUBLICATIONS

Fine et al, An open label study of oral transmucosal fentanyl citrate (OTFC) for the treatment of breakthrough cancer pain, 1991, Pain, 45, 149–153.*

Farrar JT et al. "Oral transmucosal fentanyl citrate: randomized, double–blinded, placebo–controlled trial for treatment of breakthrough pain in cancer patients", J Natl Cancer Inst (United States) Apr. 15, 1998, vol. 90, No. 8, pp 611–6.

* cited by examiner

Primary Examiner—James M. Spear
Assistant Examiner—Micah-Paul Young
(74) Attorney, Agent, or Firm—Young & Thompson

(57) ABSTRACT

A pharmaceutical composition for the treatment of acute disorders is described. The composition comprises an essentially water-free, ordered mixture of at least one pharmaceutically active agent in the form of microparticles which are adhered to the surfaces of carrier particles which are substantially larger than the particles of the active agent or agents, and are essentially water-soluble, in combination with the bioadhesion and/or mucoadhesion promoting agent. The invention also relates to a method for preparing the composition and to the use of the composition for the treatment of acute disorders.

21 Claims, 1 Drawing Sheet

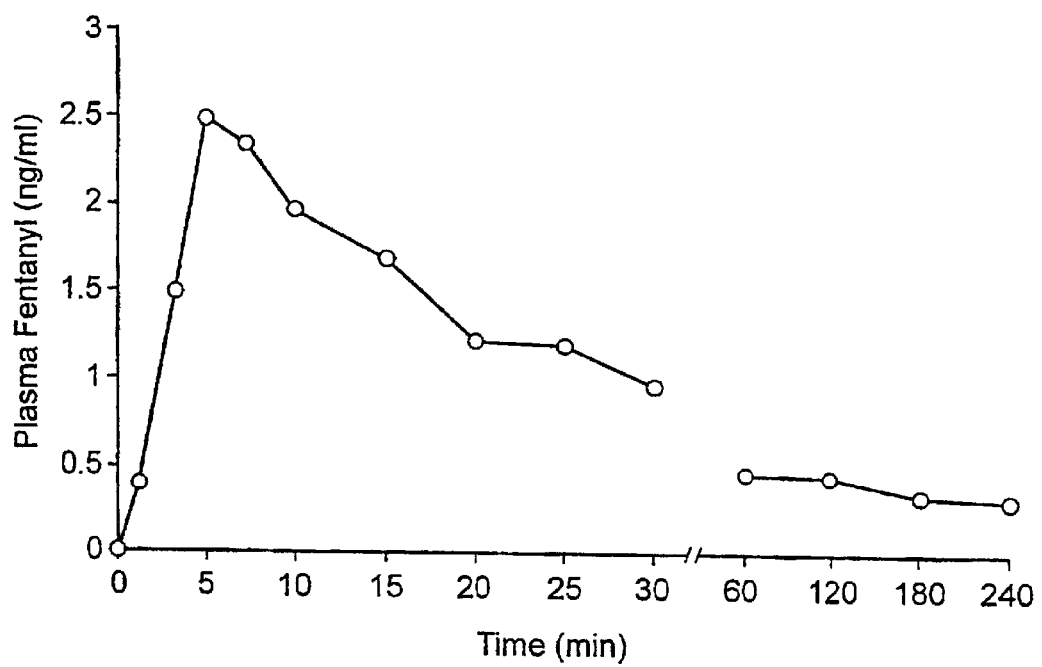

PHARMACEUTICAL COMPOSITION FOR THE TREATMENT OF ACUTE DISORDERS

FIELD OF THE INVENTION

The present invention relates to a rapidly acting pharmaceutical composition for sublingual administration of a pharmaceutical agent, to a method for preparing such a composition, and to a method for the treatment of acute disorders by the use of such a composition.

BACKGROUND OF THE INVENTION

Acute and/or severe disorders are a common cause of emergency treatment or hospitalization. One of the most common disorders of this type is acute or breakthrough pain. In cancer patients, pain is usually treated with non-steroid anti-inflammatory drugs (NSAIDs) and opiates alone or in combination. Opioid-requiring cancer pain patients are usually given slow-release opiates (slow-release morphine or ketobemidone or transdermal fentanyl). A characteristic feature of cancer pain are periods of inadequate analgesia (breakthrough pain). Most often they are due to increased physical activity of the patient. However, treatment of breakthrough pain by administration of increased time contingent doses of long-acting analgesics causes adverse side effects such an excess sedation, nausea, and constipation.

Other disorders and conditions which require a fast-acting treatment are, for example, pulmonary edema, gastroesophageal reflux, insomnia and nephrolitiasis.

Presently available oral, rectal, or sublingual formulations have relatively lengthy onset times or erratic absorption characteristics that are not well suited to control acute disorders.

Conditions of acute operative/postoperative or traumatic/posttraumatic pain as well as pain due to severe disease (e.g. myocardial infarction, nephrolithiasis, etc.) is usually treated with opioid analgesics which are administered parenterally (by intravenous or intramuscular administration) to obtain a rapid onset of analgesia. In such cases, rapid-onset oral alternatives are of considerable therapeutic interest. Also for the treatment of other acute disorders, it is of considerable interest to provide fast-acting therapeutic compositions which may be administered orally instead of parenterally or rectally.

However, many pharmaceutically active agents which would be advantageous to adminster orally are not suitable to be swallowed. They may, for example, be inactivated by the gastro-intestinal liquids, have a slow action because of a low solubility in the aqueous medium, or be highly susceptible to metabolism by gastro-intestinal enzymes and have poor absorptiom properties, as exemplified for peptide hormones. It is therefore more preferable to arrange for the active component to be taken up through the mucous membranes of the oral cavity. Here, the most preferred way of administration is via the sublingual route. In this administration, a dosage unit of the pharmaceutical composition is placed under tongue, and the active component is absorbed through the surrounding mucous membranes. However, with this way of administration the risk that the patient swallows the medication by swallowing saliva is well known.

For the treatment of acute pain may be used fentanyl, N-(1-phenethyl-4-piperidyl)-propioanilide, or one of its pharmaceutically acceptable salts. This compound is an opioid agonist and shares many of the pharmacodynamic effects of opiates such as morphine and meperidine. However, compared to these opiates, fentanyl exhibits little hypnotic activity, rarely induces histamine release, and respiratory depression is more short-lived. Fentanyl is commercially available for intravenous, intrabucchal (lozenge-transmucosal) and transdermal administration.

Following parenteral administration of fentanyl, the analgesic action is more prompt and less prolonged than that of morphine and meperidine. The onset of analgesia following i.v. administration is rapid. Peak analgesia is obtained within a few minutes. Following transbucchal administration by a lozenge, consumption of the lozenge is usually complete within 30 min and peak plasma concentrations appear after around 20 minutes, as described by e.g. Farrar et al., J. Natl. Cancer Inst., 1998, 90(8), p. 611–616. Analgesia is apparent within 5–15 min and peaks at about 20–50 min. While this is an improvement over oral administration for gastrointestinal uptake, a quicker onset of analgesia would be of substantial benefit to the patient. In addition, substantial amounts of lozenge-administered fentanyl are swallowed by the patient. This is not desirable and results in the administration of excessive amounts of the drug, which may give rise to side effects.

OBJECTS OF THE INVENTION

It is one object of the invention to provide for the treatment of acute disorders by perorally administering at least one pharmaceutically active agent in a manner giving rise to pharmacologically effective plasma levels of said agent or agents within a short time after administration.

It is another object of the invention to provide a pharmaceutical composition suitable for that purpose.

It is a further object of the invention to provide a method of making such a composition.

It is an additional object of the invention to provide a method of manufacture of a medicament for sublingual administration containing a physiologically effective dose of at least one pharmaceutically active compound useful in the treatment of acute disorders.

DESCRIPTION OF THE DRAWING

The sole FIGURE of the drawing shows the result of a test of the bioavailability of the active agent in a composition according to the invention. It is a diagram showing the plasma concentration of the agent against the time after administration.

SUMMARY OF THE INVENTION

According to the invention, the peroral treatment of acute disorders comprises sublingual administration of an ordered mixture comprising a pharmacologically effective amount of at least one pharmaceutically active agent. Said agent or agents is administered sublingually in combination with a bioadhesion and/or mucoadhesion promoting compound.

Further according to the invention, there is also provided a single-dose pharmaceutical composition for sublingual administration, comprising a pharmacologically effective amount of at least one pharmaceutically active agent. Said composition also contains a bioadhesion or mucoadhesion promoting compound. This composition reduces erratic drug absorption via swallowed saliva and enables the administration of small amounts of said agent or agents. Therefore, it substantially reduces the risk of side effects and intrapatient as well as interpatient variation of therapeutic response. Thereby the risk of drug accumulation is reduced, making the pharmaceutical preparation well suited for repeated dosing in patients suffering from acute disorders.

The amount of active agent or agents contained in the pharmaceutical composition of the invention is obviously dependent on a number of factors, which are to be evaluated by the treating physician. Among such factors may be mentioned the specific agent used and the type of disorder being treated, the medical status of the patient, and others.

When fentanyl is used for the treatment of acute or breakthrough pain, the composition of the invention should contain from 0.05 up to 20 weight percent of fentanyl or one of its pharmaceutically acceptable salts. More preferably, the compositions contains from 0.05 to 5 weight percent of fentanyl, and especially from 0.1 to 1 weight percent. The contents can also be expressed as the amount of fentanyl in a dose unit of the composition, such as a tablet. In this case, a dose unit should contain from 0.05 to 20 mg, and preferably 0.1 to 5 mg of fentanyl. When the fentanyl is used in the form of a salt, these percentages and amounts should be recalculated accordingly.

Still further according to the invention, the sublingual composition comprises an ordered mixture of one or more bioadhesive and/or mucoadhesive carrier substances coated with the pharmaceutically active agent or agents in a fine particulate form.

It is preferred to formulate the composition according to the invention by use of the technology for formulating rapidly dissolving ordered-mixture compositions disclosed in European patent EP 0 324 725. In these compositions, the drug in a finely dispersed state covers the surface of substantially larger carrier particles. Such compositions disintegrate rapidly in water, thereby dispersing their contents of microscopic drug particles.

However, this prior art technique of using an ordered mixture for rapid drug dissolution has hitherto only been reported to be suitable for conventional oral drug therapy, i.e. for solid dosage forms which are to be swallowed. For such preparations, the dissolution of the drug particles takes place in the stomach, i.e. in an environment where there exists a relatively large volume of liquid which can dissolve the drug particles. In the entire prior art literature, dissolution testing of ordered mixtures has been conducted with a large volume of water, typically 1 liter. The possibility to use ordered mixtures for sublingual administration, where the volume of liquid available as a solvent is limited to a few milliliters, has not been considered as a feasible approach. It was therefore unexpected that the present form of a solid dosage form preparation and administration route gives positive and useful results. In such an ordered mixture, the active agent or agents have a mean particle size below 10 $\mu$m. This size is determined on a weight basis, as obtained directly by e.g. dry sieving analysis, as is known by those skilled in the art.

A bioadhesion and/or mucoadhesion promoting agent is additionally added to the carrier particles according to the invention. The bioadhesion and/or mucoadhesion promoting agent is effective in making the active agent or agents adhere to the oral mucosa and may, in addition, possess properties to swell and expand in contact with water and thus make the tablet or the carrier particles disintegrate when wetted with saliva. The bio/mucoadhesion promoting agent must then be present on the surface of the carrier particles, but it may optinally also be present within these particles, as described below.

The expression "mucoadhesion" is meant to denote an adhesion to mucous membranes which are covered by mucus, such as those in the oral cavity, while the expression "bioadhesion" is meant to denote an adhesion to biological surfaces more in general, including mucous membranes which are not covered by mucus. These expressions generally overlap as definitions, and may usually be used interchangeably, although the expression "bioadhesive" has a somwhat wider scope. In the present specification and claims, the two expressions serve the same purpose as regards the objects of the invention, and this has been expressed by the use of the common term "bio/mucoadhesion".

Suitably the carrier particles contain from 0.1 up to 25 weight percent of bio/mucoadhesion promoting compound, based on the total composition. In practice, contents below 1 weight percent have been found to give an insufficient bio/mucoadhesive effect. The preferred range of bio/mucoadhesion promoting agent content is from 1 to 15 weight percent.

It is preferred that the bio/mucoadhesion promoting agent is a polymeric substance, preferably a substance with an average molecular weight above 5,000 (weight average). The level of hydration of the mucosa adhesion promoting agent interface is of importance in the development of bio/mucoadhesive forces. Therefore, the faster the swelling of the polymer, the faster is the initiation of bio/mucoadhesion. The hydration of bioadhesive compounds also makes them useful as absorption enhancers according to the invention.

Preferably, the carrier particle size is from 50 to 750 $\mu$m, and more preferredly from 100 to 600 $\mu$m. Although particle sizes outside the indicated range can be used, practical difficulties are experienced when formulating pharmaceutical preparations from particles having such sizes. The carrier used may comprise any substance which is pharmaceutically acceptable, is highly soluble in water, and which can be formulated into particles fit for incorporating a bio/mucoadhesion promoting agent. A number of such substances are known to the person skilled in this art. As suitable examples may be mentioned carbohydrates, such as sugar, mannitol and lactose, or pharmaceutically acceptable inorganic salts, such as sodium chloride or calcium phosphate.

In accordance with one particularly preferred aspect of the invention, the carrier also comprises a fragmentation promoting agent. By a fragmentation promoting agent is meant a brittle material which is readily crushed or broken up when a pharmaceutical composition of which it forms a part is compacted into tablets. If a bio/mucoadhesion promoting agent also is incorporated within the carrier as well as being added to the carrier surface, further surfaces of bio/mucoadhesion promoting agent may then exposed for hydration. This effect is especially pronounced when the bio/mucoadhesion promoting agent also serves as a disintegrant. Mannitol and lactose have been found to be particularly suitable as fragmentation promoting agents.

The addition of a pharmaceutically acceptable surfactant to the composition is also a preferred feature of the invention. The increased wetting effect of the surfactant enhances the hydration of the carrier particles, which results in faster initiation of the bio/mucoadhesion. The surfactant should be in a finely dispersed form and intimately mixed with the active agent or agents. The amount of surfactant should be from 0.5 to 5 weight percent of the composition, and preferably then from 0.5 to 3 weight percent.

As examples of suitable surfactants may be mentioned sodium lauryl sulfate, polysorbates, bile acid salts and mixtures of these.

A variety of polymers known in the art can be used as bio/mucoadhesion promoting agents. In addition to their polymeric nature, their ability to swell is important. On the other hand, it is also important that they are substantially insoluble in water. Their swelling factor by volume when brought into contact with water or saliva should preferably be at least 10, while a factor of at least 20 is more preferred. Examples of such bio/mucoadhesion promoting agents include cellulose derivatives such as hydroxypropylmethyl cellulose (HPMC), hydroxyethyl cellulose (HEC), hydroxypropyl cellulose (HPC), methyl cellulose, ethyl hydroxyethyl cellulose, carboxymethyl cellulose and sodium carboxymethyl cellulose (NaCMC); starch derivatives such as moderately cross-linked starch; acrylic polymers such as carbomer and its derivatives (Polycarbophyl, Carbopol®, etc.); polyethylene oxide (PEO); chitosan (poly(D-glucosamine)); natural polymers such as gelatin, sodium alginate, pectin; scleroglucan; xanthan gum; guar gum; poly co-(methylvinyl ether/maleic anhydride); and crosscaramellose. Combinations of two or more bio/mucoadhesive polymers can also be used. More generally, any physiologically acceptable agent showing bio/mucoadhesive characteristics may be used successfully to be incorporated in the carrier. Bio/mucoadhesiveness can be determined in vitro, e.g. according to G. Sala et al., Proceed. Int. Symp. Contr. Release. Bioact. Mat. 16:420, 1989.

Some suitable commercial sources for representative bio/mucoadhesive polymers include:

Carbopol® acrylic copolymer—BF Goodrich Chemical Co, Cleveland, Ohio, USA;
HPMC—Dow Chemical Co., Midland,), Mich., USA;
NEC (Natrosol)—Hercules Inc., Wilmington, Del., USA;
HPC (Klucel®)—Dow Chemical Co., Midland, Mich., USA;
NaCMC—Hercules Inc. Wilmington, Del. USA;
PEO—Aldrich Chemicals, USA;
Sodium Alginate,—Edward Mandell Co., Inc., Carmel, N.Y., USA;
Pectin—BF Goodrich Chemical Co., Cleveland, Ohio, USA;
Ac-Di-Sol® (modified cellulose gum with a high swellability)—FMC Corp., USA;
Actigum,—Mero-Rousselot-Satia, Baupte, France;
Satiaxane—Sanofi BioIndustries, Paris, France;
Gantrez®—ISP, Milan, Italy;
Chitosan—Sigma, St Louis, Miss., USA;

Depending on the type and the proportion of the bio/mucoadhesion promoting agent used, the rate and intensity of bio/mucoadhesion may be varied. According to one of the preferred aspects of the invention, substances with high and rapid capacity for swelling are preferred.

In order for the pharmaceutical composition of the invention to function properly when a bio/mucoadhesion promoting agent is added thereto, this agent must be positioned at the surfaces of the carrier particles. The bio/mucoadhesion promoting agent can then be admixed to the carrier particles in several ways. In a preferred embodiment of the invention, a fine particulate quality of the bio/mucoadhesion promoting agent is mixed together with the coarse carrier for a sufficient time to produce an ordered mixture, where the finer particles exist as discrete primary particles adhered to the surfaces of the carrier particles. Thus, the bio/mucoadhesion promoting agent is admixed in the same way as the active compound described in European patent No. 0 324 725.

In yet another embodiment of the invention, the bio/mucoadhesion promoting agent may, besides it peripheral orientation on the surfaces of the carrier particles, also be incorporated into the carrier particles in various ways. For example, the finely dispersed carrier can be granulated together with finely dispersed bio/mucoadhesive in a liquid which does not dissolve the bio/mucoadhesive agent or cause it to swell. In this case, the dry constituents are first mixed, and the resultant mix is then moistened with a non-dissolving/non-swelling liquid, such as absolute ethanol. The resultant mass is granulated, for instance by forcing it through a filter. It is then dried and finely ground. Alternatively, the moist mass can he dried and then granulated. Another way of producing the carrier particles according to the invention is by dissolving the carrier agent in a solvent which will not dissolve the bio/mucoadhesion promoting agent or cause it to swell, followed by the addition or the bio/mucoadhesion promoting agent to the solution, evaporation of the solvent, and granulation of the residue. Other methods are also conceivable to the person skilled in this art. Irrespective of the method applied, a suitable grain size fraction of the carrier agent containing bio/mucoadhesion promoting agent is prepared in a final stage, e.g. by passing the particulate mixtures through an screen or sieve of an appropriate mesh size, for instance a U.S. mesh size from 35 to 170.

The bio/mucoadhesion promoting agent suitably has a particle size between 1 and 100 $\mu$m. When the particles of this agent are to be mixed with the carrier particles to form an ordered mixture, their size lies within the lower part of the size interval, and suitably their size is then below 10 $\mu$m. When the bio/mucoadhesion promoting agent is to be incorporated in the carrier particles, its particle size may be within the upper part of the size interval.

The invention is particularly directed to the administration of drugs which are used for the treatment of medical conditions where a rapid and transient effect is desirable, such as pain, insomnia, allergic conditions and pulmonary oedema. As non-limiting examples of such drugs may be mentioned morphine (analgetic), fentanyl (analgetic), alfentanyl (analgetic), sufentanyl (analgetic), buprenorphine (analgetic), pizotifen (analgetic), sumatriptan (analgetic), indomethacin (analgetic), sulindac (analgetic), diclofenac (analgetic), ketorolac (analgetic), piroxicam (analgetic), tenoxicam (analgetic), ibuprofen (analgetic), naproxen (analgetic), ketoprofen (analgetic), butazolidine (analgetic), phenylbutazone (analgetic), diazepam (insomnia), oxazepam (insomnia), zopiclone (insomnia), zolpidem (insomnia), propiomazin (insomnia), valeriana (insomnia), levomepromazin (insomnia), cyclizine (allergy), cetirizine (allergy), terfenadine (allergy), acrivastine (allergy), fexofenadine (allergy) and furosemide (diuretic).

Other drugs which benefit from an enhanced absorption and which may be used for medical conditions where a rapid onset of the action is desirable include, without any limiting sense, various peptides and enzymes, such as atrial natriuretic peptides (ANP, ANF, auriculin) (diuretics), brain natriuretic peptides (diuretics), platelet aggregation inhibitors (anticoagulants), streptokinase (antocoagulant), heparin (anticoagulant), urokinase (anticoagulant), renin inhibitors (hypertension), insulin (antidiabetic), and sleep inducing peptide (insomnia).

Further examples of drugs where exposure to gastric acid has to be avoided and where the swallowing of active drug containing saliva can be minimised by means of the bio/mucoadhesive properties of the present formulations include, without any limiting sense, benzimidazole derivatives used as $H^+$, $K^+$ and ATPase inhibitors (gastric acid reduction), such as omeprazole, pantoprazole, perprazole and lansoprazole. Other H$^+$, K$^+$ and ATPase inhibitors include alyll isothiocyanate, trifluorperazide, nolinium bromide, RP 40749 and fenoctimine.

The invention is particularly suitable for the administration of fentanyl and its pharmacologically acceptable salts, such as the citrate or maleate, which are not readily soluble in water. The particles of fentanyl or salt thereof will suitably have a maximum particle size of about 24 μm but will preferably not be greater than about 10 μm. Fentanyl is caused to adhere to the carrier particles by dry mixing of the ingredients during a period of time of sufficient length. This time period can vary according to the mixing equipment used. A person skilled in the art will have no difficulty in determining by experimentation a suitable mixing time for a given combination of active substance, bio/mucoadhesion promoting agent, and carrier, by using a particular mixing equipment.

Another preferred aspect of the invention comprises the incorporation of a disintegrating agent in the composition of the invention. Such an agent which will accelerate the dispersion of the carrier particles. Examples of disintegrating agents according to the invention include cross-linked polyvinylpyrrolidone, carboxymethyl starch, natural starch, microcrystalline cellulose, cellulose gum and mixtures of these. A preferred content of disintegrating agent is from 1% to 10% of the composition. As can be seen, the definitions of the disintegrating agent and the bio/mucoadhesion promoting agent overlap somewhat, and it may be preferred that both functions are served by the same substance. However, it is important to note that these two categories of excipients are not equivalent, and there are efficiently functioning disintegrants which do not possess bio/mucoadhesive properties, and vice versa.

The ordered mixtures prepared in accordance with the present invention can be incorporated into various kinds of pharmaceutical preparations intended for sublingual administration. Irrespective of the form given to the preparation, it is important that the preparation is essentially free from water, since its bio/mucoadhesion promoting character results from its practically instantaneous hydration when brought into contact with water or saliva. Premature hydration would drastically decrease the mucoadhesion promoting properties and result in a premature dissolution of the active substance.

A pharmaceutical composition for the preferred sublingual route of administration can be obtained by combining an aforementioned ordered mixture with conventional pharmaceutical additives and excipients used in the art for sublingual preparations. Appropriate formulation methods are well known to the person skilled in the art; see, for instance, Pharmaceutical Dosage Forms: Tablets. Volume 1, 2nd Edition, Lieberman H A et al.; Eds.; Marcel Dekker, New York and Basel 1989, p. 354–356, and literature cited therein. Suitable additives comprise additional carrier agents, preservatives, lubricants, gliding agents, disintegrants, flavorings, and dyestuffs.

Thus, the invention provides a dosage form which is easy and inexpensive to manufacture, enables rapid active substance release, promotes a rapid uptake of the active agent or agents through the oral mucosa, and enhances the upptake of otherwise poorly soluble substances, such as peptides. The use of a low dose of active agent is provided for, supporting a short duration of action while enabling a repeated dosing schedule for patients in need of treatment of recurrent acute disorders.

The invention will now be illustrated in more detail by reference to examples showing preferred but not limiting embodiments.

EXAMPLE 1

Preparation of a Rapidly Disintegrating Tablet with Bio/Mucoadhesion Promoting Properties A batch of 1000 tablets was produced from the following compositions: 81.5 g of mannitol and 2.0 g of Ac-Di-Sol® (disintegrant and bio/mucoadhesion promoting agent) were mixed with about 170 ml of absolute ethanol. The dried mixture was forced through a metal sieve of 1 mm mesh width and the resultant fraction, having a particle size from about 250 to 450 microns, was mixed with 500 mg of micronized fentanyl and with 1.0 g of finely ground sodium lauryl sulfate (surfactant) over a period of 50 hours. The resulting mixture was admixed with 5.0 g of Avicel® Ph 101 and 10.0 g sodium alginate (bio/mucoadhesion promoting agent and disintegrant) over a period of 60 minutes. The resulting mixture was compacted into tablets at a compaction pressure of 200 MPa, each tablet having a weight of 100 mg and containing 0.5 mg of fentanyl.

The dissolution rate of the tablets thus produced was investigated in accordance with USP XXIII (Paddle Method) at two different stirring speeds, 25 and 100 rpm.

EXAMPLE 2

Preparation of a Rapidly Disintegrating Tablet with Bio/Mucoadhesion Promoting Properties A batch of 1000 tablets was produced from the following composition: 91.0 g of mannitol (granular quality of a particle size from 250 to 450 μm) and 1.0 g of sodium lauryl sulfate and 500 mg of micronized fentanyl were mixed in a V-mixer over a period of 24 hours. Thereafter, 5.0 g of Avicel® PH 101 and 2.0 g of Ac-Di-Sol® (here used both as a disintegrant and as a bio/mucoadhesion promoting agent) was admixed for an additional 2 hours. Finally, 0.5 g of magnesium stearate was admixed for 2 minutes. The resulting tablet mass was compacted into tablets at a compaction pressure of 130 Mpa, each tablet containing 0.5 mg of fentanyl.

The disintegration time was tested with the use of the apparatus described in Ph. Eur. (latest edition)

It was found that the disintegration time was less than 15 seconds.

For comparison, conventional rapidly dissolving tablets were also produced. Dry mannitol having a particle size of 250–450 microns was dry mixed with micronized fentanyl without any further addition of excipients. The mixing time was 50 hours. The resulting mixture was compacted into tablets at a compaction pressure of 200 MPa, each tablet containing 0.5 mg of fentanyl.

The results from this investigation showed that the ordered mixture with bio/mucoadhesive properties according to the invention (Example 1) has a dissolution rate equal to that of a conventional rapidly dissolving tablet formulation. The entire tablet was dissolved within 2 minutes. Furthermore, the rapid disintegration found for the tablets of Example 2 was equal to or better than for the conventional tablets.

EXAMPLE 3

Evaluation of Uptake in Sublingual Administration

To one patient suffering from breakthrough pain due to cancer was administered 400 μg of fentanyl as a sublingual tablet formulated as described in Example 1. The plasma concentration of fentanyl was monitored for a time of 240 minutes after the administration, and the results are shown in the accompanying FIGURE. It will be seen that the uptake of fentanyl was rapid, with the maximum value attained already after 5 minutes. This shows that a sublingual preparation according to the invention gives a rapid uptake of the active agent, even though a very small volume of liquid is available for dissolution in this route of administration.

EXAMPLE 4

Evaluation of Bio/Mucoadhesive Properties

For in vitro evaluation of the bio/mucoadhesive properties of the formulation according to the present invention, a method permitting evaluation of bio/mucoadhesion promoting properties directly on finished dosage forms (Sala, G. E. et al., Proc. Int. Symp. Contr. Release Bioact. Mat. 16:420, 1989) was used. The evaluation was based on measurements of the flow of water required to remove the active substance from a rabbit intestinal membrane. A strip of rabbit mucosa was placed horizontally in a suitable temperature controlled chamber set at 37° C. The tissue was first washed with predetermined volumes of water by means of a peristaltic pump. Pre-compressed compositions according to Example 1 (5–15 mg) were then placed on the tissue and allowed to remain there for 2 minutes to ensure proper dissolution. Upon this followed an elution with water fed by a peristaltic pump during 10 minutes. Rinsed-off fentanyl was collected, and its amount determined by radioimmunoassay (RIA) in order to establish the percentage of fentanyl removed. Subsequent tests were carried out using increasing elution flow rates. The results are shown in Table 2; percentages of removal at a high flow rate are listed for.

A Bio/mucoadhesive mixture according to the invention (Example 1);

B Bio/mucoadhesive mixture according to the invention (Example 2);

C Conventional mixture for rapid dissolution containing no bio/mucoadhesion promoting agent.

TABLE 2

|                    | % fentanyl removed |      |      |
| ------------------ | ------------------ | ---- | ---- |
| Flow rate (ml/min) | A                  | B    | C    |
| >15                | <50                | <50  | >95  |

EXAMPLE 5

Preparation of Rapidly Disintegrating Tablets for the Administration of Furosemide Rapidly disintegrating tablets with bio/mucoadhesive properties for sublingual administration were prepared according to Example 1, each tablet containing 20 mg of furosemide. The tablets show a rapid release of furosemide and a promoted uptake of furosemide through the oral mucosa in comparison with conventional peroral formulations. The preparation may be used for the treatment of pulmonary edema.

EXAMPLE 6

Preparation of Rapidly Disintegrating Tablets for the Administration of Atrial Natriuretic Peptide (ANP)

Rapidly disintegrating tablets with bio/mucoadhesive properties which in addition enhance absorption of large molecules in sublingual administration were prepared according to Example 1, each tablet containing 0.7 mg ANP. The tablets show a rapid release of ANP and an enhanced uptake of ANP through the oral mucosa in comparison with conventional peroral formulations. The preparation may be used for the treatment of pulmonary edema.

EXAMPLE 7

Preparation of Rapidly Disintegrating Tablets for the Administration of Omeprazole Rapidly disintegrating tablets with bio/mucoadhesive properties for sublingual administration were prepared according to example 1, each tablet containong 10 mg of omeprazole. The tablets show a rapid release of omeprazole and an enhanced uptake of omeprazole through the oral mucosa, as well as a reduced swallowing of omeprazole in the saliva, in comparison with conventional peroral formulations. The preparation may be used for the treatment of gastroesophageal reflux.

EXAMPLE 8

Preparation of Rapidly Disintegrating Tablets for the Administration of Diclofenac Rapidly disintegrating tablets with bio/mucoadhesive properties for sublingual administration were prepared according to example 1, each tablet containinh 50 mg of diclofenac. The tablets show a rapid release of diclofenac and an enhanced uptake of diclofenac through the oral mucosa in comparison with conventional peroral formulations. The preparation may be used for the treatment of painful conditions such as neprolithiasis.

In the foregoing specification, the present invention has been described with reference to various examples and preferred embodiments. However, for a person skilled in the art, it is clear that the scope of the invention is not limited to these examples and embodiments, and that further modifications and variations are possible without departing from the inventive idea, The scope of the invention is thus only limited by the appended claims.

What is claimed is:

1. A pharmaceutical composition for the treatment of acute disorders by sublingual administration, comprising an essentially water-free, ordered mixture of microparticles of at least one pharmaceutically active agent adhered to the surfaces of carrier particles, said particles being substantially larger than said microparticles and being water-soluble, and a bioadhesion and/or mucoadhesion promoting agent mainly adhered to the surfaces of the carrier particles.

2. A composition according to claim 1, wherein the microparticles of said active agent or agents have a weight based mean diameter of less than 10 $\mu$m.

3. A composition according to claim 1, wherein the mean sieve diameter of the carrier particles is between 100 and 600 $\mu$m.

4. A composition according to claim 1, wherein the carrier particles comprise a brittle material which will fragmentize easily when compressed.

5. A composition according to claim 1, wherein the carrier particles contain from 0.1 to 25 weight percent of the bio/mucoadhesion promoting agent.

6. A composition according to claim 5, wherein the bio/mucoadhesion promoting agent is selected from the group consisting of acrylic polymers, cellulose derivatives, natural polymers having bio/mucoadhesive properties, and mixtures thereof.

7. A composition according to claim 6, wherein the bio/mucoadhesion promoting agent is selected from the group consisting of cellulose derivatives and comprising hydroxypropylmethyl cellulose, hydroxyethyl cellulose, hydroxypropyl cellulose, sodium carboxymethyl cellulose, methyl cellulose, ethyl hydroxyethyl cellulose, carboxymethyl cellulose, and modified cellulose gum; crosscaramellose; modified starch; acrylic polymers comprising carbomer and its derivatives; polyethylene oxide; chitosan; gelatin; sodium alginate; pectin; scleroglucan; xanthan gum; guar gum; poly-co-(methyl vinyl ether-maleic anhydride); and mixtures thereof.

8. A composition according to claim 1, further comprising a pharmaceutically acceptable surfactant in a finely dispersed form and intimately mixed with the active agent or agents.

9. A composition according to claim 8, wherein the surfactant is present in an amount from 0.5 to 5 weight percent of the composition.

10. A composition according to claim 8, wherein the surfactant is selected from the group consisting of sodium lauryl sulfate polysorbates, bile acid salts and mixtures thereof.

11. A composition according to claim 1, wherein the carrier particles comprise a water-soluble, pharmaceutically acceptable carbohydrate and/or an inorganic salt.

12. A composition according to claim 11, wherein the carrier particles comprise at least one of the materials mannitol, lactose, calcium phosphate and sugar.

13. A composition according to claim 1, wherein the carrier particles contain at least one pharmaceutical disintegrating agent promoting the dispersion of the microparticles of the active agent or agents over the sublingual mucosa.

14. A composition according to claim 13, wherein the disintegrating agent is selected from the group consisting of cross-linked polyvinylpyrrolidone, carboxymethyl starch, natural starch, microcrystalline cellulose, cellulose gum, and mixtures thereof.

15. A composition according to claim 13, wherein the disintegrating agent is present in an amount from 1 to 10 weight percent of the composition.

16. A composition according to claim 1, wherein the pharmaceutically active agent is fentanyl or a pharmaceutically acceptable salt thereof.

17. A composition according to claim 1, for the treatment of acute disorders by sublingual administration.

18. A composition according to claim 16, for the treatment of acute or breakthrough pain by sublingual administration of fentanyl or a pharmaceutically acceptable salt thereof.

19. A method for the treatment of acute disorders, wherein to an individual afflicted with said disorder is administered sublingually at least one dose unit of an essentially water-free pharmaceutical composition containing an effective amount of at least one pharmaceutically active agent in the form of microparticles adhered to the surfaces of carrier particles, which are substantially larger than said microparticles and are essentially water-soluble, and a bioadhesion and/or mucoadhesion promoting agent.

20. A method according to claim 19, wherein the pharmaceutically active agent is fentanyl or a pharmaceutically acceptable salt thereof.

21. A method according to claim 20, wherein the fentanyl is administered in an amount from 0.05 to 20 mg.

* * * * *